(12) United States Patent
Van Spreuwel-Goossens et al.

(10) Patent No.: US 11,033,660 B2
(45) Date of Patent: Jun. 15, 2021

(54) METHOD FOR PRODUCING POROUS GELATIN SHEET, POROUS GELATIN SHEET, AND USE THEREOF

(71) Applicant: FUJIFILM CORPORATION, Tokyo (JP)

(72) Inventors: Carolina Antonia Francina Maria Van Spreuwel-Goossens, Tilburg (NL); Huibert Albertus Van Boxtel, Tilburg (NL); Sebastianus Gerardus Johannes Maria Kluijtmans, Tilburg (NL)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/165,768

(22) Filed: Oct. 19, 2018

(65) Prior Publication Data
US 2019/0117847 A1 Apr. 25, 2019

Related U.S. Application Data

(63) Continuation of application No. PCT/JP2017/015990, filed on Apr. 21, 2017.

(30) Foreign Application Priority Data

Apr. 21, 2016 (GB) ..................................... 1606939

(51) Int. Cl.
*A61L 27/56* (2006.01)
*A61L 27/22* (2006.01)
(Continued)

(52) U.S. Cl.
CPC .............. *A61L 27/56* (2013.01); *A61L 27/222* (2013.01); *A61L 27/227* (2013.01); *A61L 27/38* (2013.01);
(Continued)

(58) Field of Classification Search
CPC ........ A61L 27/56; A61L 27/38; A61L 27/227; A61L 27/3895; A61L 27/58; A61L 27/222; C12N 15/09; A61K 35/12
See application file for complete search history.

(56) References Cited

U.S. PATENT DOCUMENTS

2005/0147646 A1   7/2005  Nilsson
2006/0241032 A1  10/2006  Bouwstra et al.
(Continued)

FOREIGN PATENT DOCUMENTS

CN   103834057 B   2/2016
EP      1801122 A1  6/2007
(Continued)

OTHER PUBLICATIONS

Ogiwara et al. (WO2014115732A1 Machine Translation) (Year: 2014).*

(Continued)

*Primary Examiner* — Aradhana Sasan
*Assistant Examiner* — Quanglong N Truong
(74) *Attorney, Agent, or Firm* — Birch, Stewart, Kolasch & Birch, LLP

(57) ABSTRACT

The object of the present invention is to provide a method for producing a porous gelatin sheet having cell proliferation properties; a porous gelatin sheet having cell proliferation properties; and use thereof. According to the present invention, there is provides a method for producing a porous gelatin sheet that includes chambers, in which at least half of the chambers are spherical, and/or at least half of the chambers have a diameter that is within ±30% of an average chamber diameter, and the chambers have an average diameter of less than 100 μm.

19 Claims, 2 Drawing Sheets

Specification includes a Sequence Listing.

(51) Int. Cl.
  *A61L 27/38*   (2006.01)
  *C12N 15/09*   (2006.01)
  *A61L 27/58*   (2006.01)
  *A61K 35/12*   (2015.01)
(52) U.S. Cl.
  CPC ............ *A61L 27/3895* (2013.01); *A61L 27/58* (2013.01); *C12N 15/09* (2013.01); *A61K 35/12* (2013.01)

(56) References Cited

U.S. PATENT DOCUMENTS

| | | |
|---|---|---|
| 2008/0213564 A1 | 9/2008 | Ma et al. |
| 2009/0246282 A1 | 10/2009 | Kluijtmans et al. |
| 2014/0161843 A1 | 6/2014 | Yang et al. |
| 2016/0106884 A1 | 4/2016 | Lao et al. |
| 2017/0095595 A1 | 4/2017 | Nakamura |
| 2017/0304458 A1 | 10/2017 | Van Spreuwel-Goossens |

FOREIGN PATENT DOCUMENTS

| | | |
|---|---|---|
| JP | 2005-529598 A | 10/2005 |
| JP | 2007-297401 A | 11/2007 |
| JP | 2009-520501 A | 5/2009 |
| WO | WO 03/104313 A1 | 12/2003 |
| WO | WO 2014/195864 A1 | 12/2014 |
| WO | WO 2015/194494 A1 | 12/2015 |
| WO | WO 2016/063935 A1 | 4/2016 |

OTHER PUBLICATIONS

International Preliminary Report on Patentability and Written Opinion dated Nov. 1, 2018 in PCT/JP2017/015990 (with English Translation).
International Search Report dated Aug. 1, 2017 in PCT/JP2017/015990 (with English translation).
Extended European Search Report dated Mar. 29, 2019, for corresponding European Application No. 17786047.5.
Japanese Office Action for corresponding Japanese Application No. 2018-513224, dated Sep. 17, 2019, with English translation.
European Office Action dated Mar. 11, 2020, for corresponding European Patent Application No. 17786047.5.
European Office Action, dated Dec. 16, 2020, for corresponding European Application No. 17786047 5.

* cited by examiner

SEQUENCE LISTING

```
<160> NUMBER OF SEQ ID NOS: 1

<210> SEQ ID NO 1
<211> LENGTH: 571
<212> TYPE: PRT
<213> ORGANISM: Artificial Sequence
<220> FEATURE:
<223> OTHER INFORMATION: Synthetic: Recombinant sequence

<400> SEQUENCE: 1

Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Ala Gly Pro Lys Gly Ala Asp Gly Ala Pro Gly Ala Pro
        35                  40                  45

Gly Leu Gln Gly Met Pro Gly Glu Arg Gly Ala Ala Gly Leu Pro Gly
    50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
            100                 105                 110

Asp Ala Gly Pro Lys Gly Ala Asp Gly Ala Pro Gly Lys Asp Gly Val
        115                 120                 125

Arg Gly Leu Ala Gly Pro Ile Gly Pro Pro Gly Pro Ala Gly Ala Pro
    130                 135                 140

Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Ala Gly Pro Lys Gly Ala
                165                 170                 175
```

-continued

```
Asp Gly Ala Pro Gly Lys Asp Gly Val Arg Gly Leu Ala Gly Pro Pro
            180                 185                 190
Gly Ala Pro Gly Leu Gln Gly Ala Pro Gly Leu Gln Gly Met Pro Gly
            195                 200                 205
Glu Arg Gly Ala Ala Gly Leu Pro Gly Pro Lys Gly Glu Arg Gly Asp
            210                 215                 220
Ala Gly Pro Lys Gly Ala Asp Gly Ala Pro Gly Ala Pro Gly Leu Gln
225                 230                 235                 240
Gly Met Pro Gly Glu Arg Gly Ala Ala Gly Leu Pro Gly Pro Lys Gly
                245                 250                 255
Glu Arg Gly Asp Ala Gly Pro Lys Gly Ala Asp Gly Ala Pro Gly Lys
            260                 265                 270
Asp Gly Val Arg Gly Leu Ala Gly Pro Ile Gly Pro Pro Gly Glu Arg
            275                 280                 285
Gly Ala Ala Gly Leu Pro Gly Pro Lys Gly Glu Arg Gly Asp Ala Gly
            290                 295                 300
Pro Lys Gly Ala Asp Gly Ala Pro Gly Lys Asp Gly Val Arg Gly Leu
305                 310                 315                 320
Ala Gly Pro Ile Gly Pro Pro Gly Pro Ala Gly Ala Pro Gly Ala Pro
                325                 330                 335
Gly Leu Gln Gly Met Pro Gly Glu Arg Gly Ala Ala Gly Leu Pro Gly
            340                 345                 350
Pro Lys Gly Glu Arg Gly Asp Ala Gly Pro Lys Gly Ala Asp Gly Ala
            355                 360                 365
Pro Gly Lys Asp Gly Val Arg Gly Leu Ala Gly Pro Pro Gly Ala Pro
            370                 375                 380
Gly Leu Gln Gly Ala Pro Gly Leu Gln Gly Met Pro Gly Glu Arg Gly
385                 390                 395                 400
Ala Ala Gly Leu Pro Gly Pro Lys Gly Glu Arg Gly Asp Ala Gly Pro
                405                 410                 415
Lys Gly Ala Asp Gly Ala Pro Gly Ala Pro Gly Leu Gln Gly Met Pro
            420                 425                 430
Gly Glu Arg Gly Ala Ala Gly Leu Pro Gly Pro Lys Gly Glu Arg Gly
            435                 440                 445
Asp Ala Gly Pro Lys Gly Ala Asp Gly Ala Pro Gly Lys Asp Gly Val
            450                 455                 460
Arg Gly Leu Ala Gly Pro Ile Gly Pro Pro Gly Glu Arg Gly Ala Ala
465                 470                 475                 480
Gly Leu Pro Gly Pro Lys Gly Glu Arg Gly Asp Ala Gly Pro Lys Gly
                485                 490                 495
Ala Asp Gly Ala Pro Gly Lys Asp Gly Val Arg Gly Leu Ala Gly Pro
            500                 505                 510
Ile Gly Pro Pro Gly Pro Ala Gly Ala Pro Gly Ala Pro Gly Leu Gln
            515                 520                 525
Gly Met Pro Gly Glu Arg Gly Ala Ala Gly Leu Pro Gly Pro Lys Gly
            530                 535                 540
Glu Arg Gly Asp Ala Gly Pro Lys Gly Ala Asp Gly Ala Pro Gly Lys
545                 550                 555                 560
Asp Gly Val Arg Gly Leu Ala Gly Pro Pro Gly
                565                 570
```

US 11,033,660 B2

METHOD FOR PRODUCING POROUS GELATIN SHEET, POROUS GELATIN SHEET, AND USE THEREOF

CROSS-REFERENCE TO RELATED APPLICATIONS

This application is a Continuation of PCT International Application No. PCT/JP2017/015990 filed on Apr. 21, 2017, which claims priority under 35 U.S.C. § 119(a) to GB Patent Application No. 1606939.5 filed on Apr. 21, 2016. Each of the above application(s) is hereby expressly incorporated by reference, in its entirety, into the present application.

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "2018-12-15 2870-0705PUS1 ST25.txt" created on Dec. 15, 2018 and is 5,441 bytes in size. The sequence listing contained in this .txt file is part of the specification and is hereby incorporated by reference herein in its entirety.

BACKGROUND OF THE INVENTION

1. Field of the Invention

The present invention relates to a method for producing a porous gelatin sheet. Further, the present invention relates to a porous gelatin sheet and use thereof, and a porous gelatin sheet-cell composite.

2. Description of the Related Art

In a case where the human or animal body is injured, minor amounts of tissue damage can usually be repaired by the body's own (intrinsic) repair mechanism. However, injuries involving severe tissue damage, such as myocardial infarction or trauma, often exceed the regenerative capacity of the body. There is a need for treatments which assist tissue repair in cases of severe tissue damage.

WO2016/063935A discloses microcarriers, but there is no description of a sheet.

US2008/0213564A discloses production of a gelatin foam having spherical chambers and fibrous pore walls using a paraffin spherical material of 150 µm or more, but there is no description of the size distribution of the chambers.

WO03/104313A discloses production of a spherical material by a double emulsification method using two emulsifying agents, but a single emulsifying agent is not used in the production.

WO2014/195864A discloses a pore structure having a pore size of 100 µm to 900 µm.

US2014/0161843A discloses production of a porous structure using three different biocompatible porogens and cells in an emulsification step. The average pore diameter is more than 10, 20, 40, 80, 100, or 200 µm and/or less than 500, 300, 200, 100, 80, 40, or 20 µm. In US2014/0161843A, in a case where a porous structure is produced, cells are used.

SUMMARY OF THE INVENTION

One of the problems arising from a wide range of tissue injuries is how to close or fill the resultant void or hole. With this problem in mind, scaffolds can be used as (semi) permanent fillers to pack the void or hole where tissue is missing. Scaffolds can also be used as slow-release depots to release growth factors, drugs or the like, or to deliver cells. Delivery of cells can be achieved by pre-seeding the desired cells onto a scaffold before injection or implantation into the body.

An object of the present invention to be achieved is to provide a method for producing a porous gelatin sheet having cell proliferation properties, a porous gelatin sheet having cell proliferation properties, and use thereof.

In the studies of the present inventors, the present inventors have been attempting to produce a porous sheet having good cell proliferation properties which may be used for wound repair, for example, as a scaffold or filler for packing voids. The present inventors have surprisingly found that the sheet defined in a first aspect of the present invention, as described below, have particularly good cell proliferation properties.

According to the present invention, the following inventions are provided.

<1> A method for producing a porous gelatin sheet including chambers, the method comprising the steps of:
(a) mixing a composition including water, a gelatin, a water-immiscible liquid, and an emulsifying agent to obtain an emulsion;
(b) casting the emulsion having a temperature higher than a temperature at which the gelatin present in the composition forms a gel onto a support;
(c) cooling the emulsion present on the support to a temperature lower than a gelation point of the gelatin present in the composition;
(d) removing the water-immiscible liquid from the gelatin; and
(e) drying the gelatin to provide a porous gelatin sheet,
in which at least half of the chambers are spherical and/or at least half of the chambers have a diameter within ±30% of an average chamber diameter, and the average chamber diameter is less than 100 µm.

<2> The method according to <1>, in which steps (a) to (e) are cell-free steps.

<3> The method according to <1> or <2>, in which the emulsifying agent has an HLB of 9 or more.

<4> The method according to any one of <1> to <3>, in which the sheet further includes a network of pores which interconnect the chambers and provide passageways for cells to enter the chambers.

<5> The method according to any one of <1> to <4>, in which the sheet has a porosity of at least 50 vol %.

<6> The method according to any one of <1> to <5>, in which the sheet has an average pore diameter of at least 5 µm.

<7> The method according to any one of <1> to <6>, in which the sheet has a density of 0.04 to 0.5 g/cm³.

<8> The method according to any one of <1> to <7>, in which the sheet has a volume of 2 to 25 cm³/g.

<9> The method according to any one of <1> to <8>, in which the sheet has a porosity of at least 50 vol %, and the sheet includes pores having an average diameter of at least 5 µm,
(i) at least half of the chambers are spherical, and
(ii) at least 80% of the chambers have a diameter within ±30% of the average chamber diameter.

<10> The method according to any one of <1> to <9>, in which the sheet has a porosity of at least 50 vol %, the sheet includes surface pores having an average diameter of at least 5 and at least half of the chambers have a diameter within ±30% of the average chamber diameter.

<11> The method according to any one of <1> to <10>, in which at least 50% of the chambers are spherical.

<12> The method according to any one of <1> to <11>, in which the gelatin is a recombinant gelatin.

<13> The method according to any one of <1> to <12>, in which the gelatin is a recombinant gelatin having an isoelectric point of at least 5.

<14> The method according to any one of <1> to <13>, in which the gelatin is a recombinant gelatin including at least three RGD motifs.

<15> The method according to any one of <1> to <14>, in which the gelatin is a recombinant gelatin including at least two lysine residues, the lysine residues are extreme lysine residues, a first extreme lysine residue is a lysine residue that is closest to an N-terminus of the gelatin, a second extreme lysine residue is a lysine residue that is closest to a C-terminus of the gelatin, and the extreme lysine residues are separated by at least 25% of the total number of amino acid residues of the gelatin.

<16> A porous gelatin sheet produced by the method according to any one of <1> to <15>.

<17> Use of the porous gelatin sheet according to <16> as a cell carrier.

<18> Use of the porous gelatin sheet according to <16> as a scaffold for repairing tissue damage.

<19> A composite comprising: the porous gelatin sheet according to <16>; and live cells.

<17A> The porous gelatin sheet according to <16> to be used as a cell carrier.

<17B> A method for treating a subject comprising: administering the porous gelatin sheet according to <16> to a subject as a cell carrier.

<18A> The porous gelatin sheet according to <16> to be used as a scaffold for repairing tissue damage.

<18B> A method for repairing tissue damage comprising: administering the porous gelatin sheet according to <16> to a subject as a scaffold for repairing tissue damage.

According to the method for producing a porous gelatin sheet of the present invention, it is possible to produce a porous gelatin sheet with only a one emulsification step.

DESCRIPTION OF THE PREFERRED EMBODIMENTS

Figure 1A:
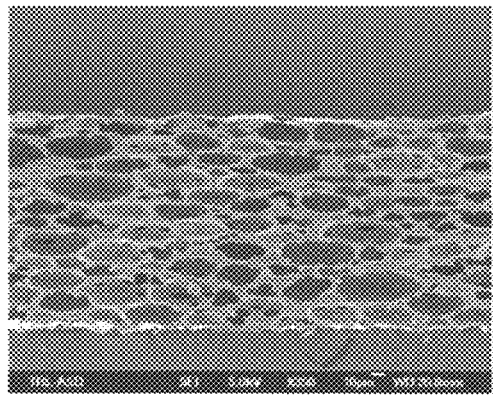
FIGS. 1A to 1D are scanning electron microscope ("SEM") photographs of cross sections of sheets of the present invention.

FIG. 1A is a SEM photograph of a cross section of a sheet of an embodiment of the present invention taken at ×350 magnification. The sheet in FIG. 1A has a thickness of 140 μm.

Figure 1B:
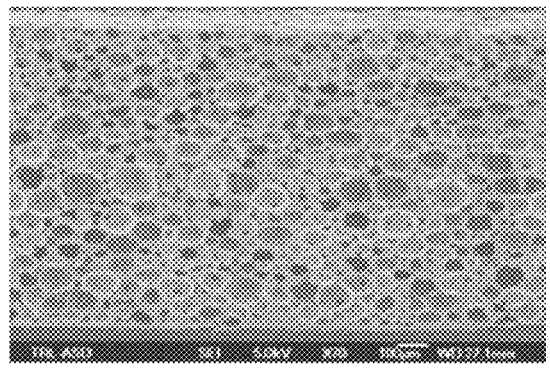

FIG. 1B is a SEM photograph of a cross section of a sheet of an embodiment of the present invention taken at ×70 magnification. The sheet in FIG. 1B has a thickness of 900 μm.

Figure 1C:
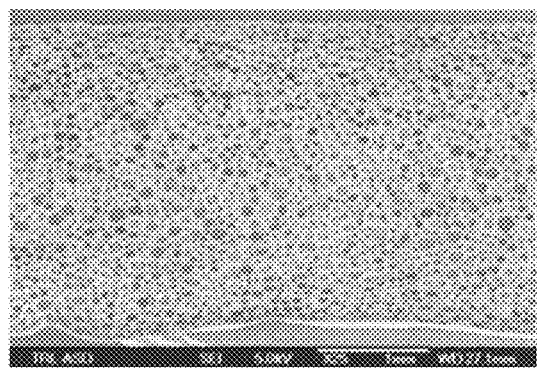

FIG. 1C is a SEM photograph of a cross section of a sheet of an embodiment of the present invention taken at ×25 magnification. The sheet in FIG. 1C has a thickness of 2500 μm.

Figure 1D:
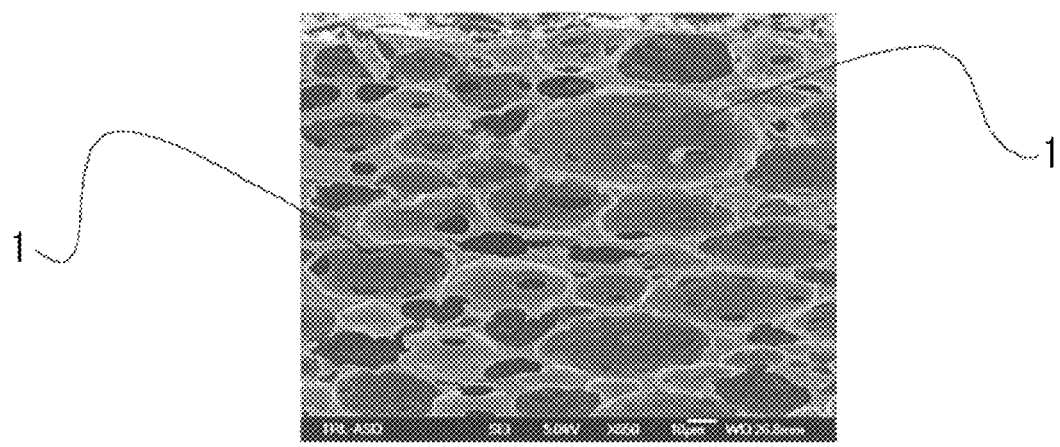

FIG. 1D is a SEM photograph of a cross section of a sheet of an embodiment of the present invention taken at ×650 magnification. The sheet in FIG. 1D has a thickness of 140 μm.

Figure 2:
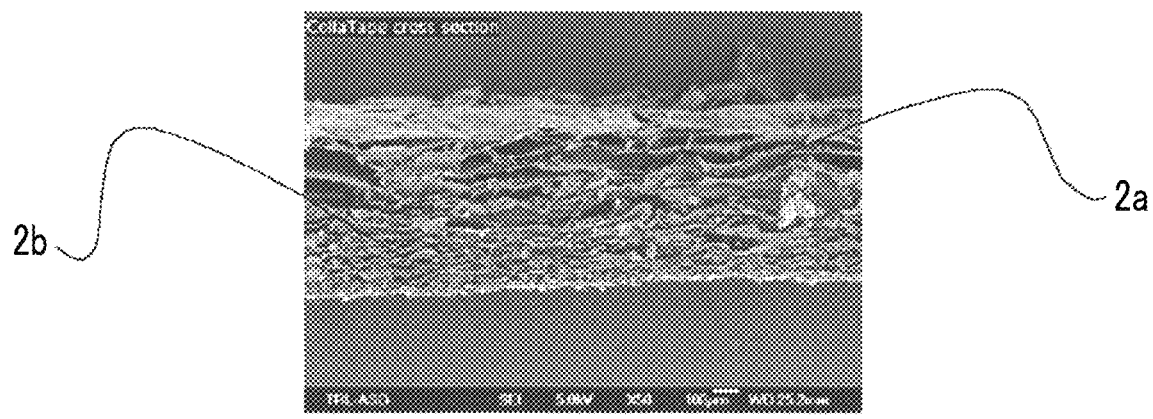
FIG. 2 is a SEM photograph of a cross section of commercially available Zimmer CollaTape (registered trade mark) (Comparative Example).

FIG. 2 is a SEM photograph of a cross section of a CollaTape (registered trade mark) base material commercially available from Zimmer Dental, taken at ×85 magnification. The sheet in FIG. 2 has a thickness of 700 μm.

The sheets shown in FIGS. 1A, 1B, and 1C are precisely flat and include spherical chambers with a uniform chamber size distribution and at least half of the chambers have a diameter within ±30% of an average chamber diameter.

The sheet shown in FIG. 1D includes spherical chambers at least half of which are spherical and at least half of which have a diameter within ±30% of the average chamber diameter.

Note that the chambers (1) in the sheet of FIG. 1D have a more uniform size and shape than those of the chambers visible in the sheet shown in Comparative Example shown in FIG. 2.

The sheet shown in FIG. 2 (Comparative Example) includes highly irregular chambers of amorphous shape, the chambers are generally large at a top side (2a) of the sheet and small at a bottom side (2b) of the sheet.

The sheets of the embodiments of the present invention provide a support for cell cultures and provide for particularly good cell proliferation in terms of rate of cell growth and the amount of cells grown.

Preferably, the sheet is flexible, foldable, and capable of being cut using scissors.

As described above, the chambers (2a and 2b) present in the commercially available sheet shown in FIG. 2 are irregular and amorphous in shape and have wide range of diameters compared to the chambers shown in the sheets of the embodiments of the present invention in FIGS. 1A to 1D.

The term "gelatin" as used in this specification includes collagen. The gelatin preferably has an average molecular weight of less than 150 kDa, and preferably of less than 100 kDa. Preferably the gelatin has an average molecular weight of at least 5 kDa, preferably at least 10 kDa, and more preferably at least 30 kDa. Preferable average molecular weight ranges for a recombinant gelatin include 50 kDa to 100 kDa, 20 kDa to 75 kDa, and 5 kDa to 40 kDa. Lower molecular weights may be preferable in a case where higher mass concentrations of gelatins are required because of the lower viscosity. The molecular weight of the gelatin may be determined by gel permeation chromatography.

The gelatin is preferably a recombinant gelatin. Recombinant gelatins may be obtained commercially from, for example, Fujifilm Corporation. Recombinant gelatins may be prepared by known methods, for example, as described in patent applications EP0926543A and EP1014176A, the contents of which are incorporated in the specification by reference. The methodology for preparing recombinant gelatins is also described in the publication "High yield secretion of recombinant gelatins by *Pichia pastoris*", M. W. T. Werten et al., Yeast 15, 1087 to 1096 (1999). Suitable recombinant gelatins are also described in WO2004/085473A.

In one embodiment, the recombinant gelatin includes at least two lysine residues, the lysine residues are extreme lysine residues. A first extreme lysine residue is a lysine residue that is closest to the N-terminus of the gelatin, a second extreme lysine residue is a lysine residue that is closest to the C-terminus of the gelatin, and the extreme lysine residues are separated by at least 25% of the total number of amino acids in the gelatin. Such recombinant gelatins may be obtained by, for example, the methods described in US2009/0246282A.

In a further embodiment of the present invention, the recombinant gelatin includes at least two amino acid residues, the two amino acid residues are extreme amino acid residues, which each independently are selected from an aspartic acid residue and a glutamic acid residue, in which a first aspartic acid residue or glutamic acid residue is an aspartic acid residue or glutamic acid residue that is closest to the N-terminus of the polypeptide, a second extreme aspartic acid residue or glutamic acid residue is an aspartic acid residue or glutamic acid residue that is closest to the C-terminus of the polypeptide, and the extreme aspartic acid residues and/or glutamic acid residues are separated by at least 25% of the total number of amino acids in the recombinant gelatin polypeptide.

Further, in yet a further embodiment, the recombinant gelatin includes at least one aspartic acid residue and/or glutamic acid residue between the extreme aspartic acid residues and/or glutamic acid residues.

In a preferred embodiment, the gelatin has excellent cell attachment properties and preferably does not display any health-related risks. Advantageously, this is achieved by using an RGD-enriched recombinant gelatin, for example, a recombinant gelatin in which the percentage of RGD motifs relative to the total number of amino acids is at least 0.4. In a case where the RGD-enriched gelatin includes 350 amino acids or more, each stretch of 350 amino acids preferably contains at least one RGD motif. Preferably, the percentage of RGD motifs relative to the total number of amino acids is at least 0.6, more preferably at least 0.8, more preferably at least 1.0, more preferably at least 1.2, and most preferably at least 1.5.

A percentage RGD motifs of 0.4 corresponds with at least one RGD sequence per 250 amino acids. The number of RGD motifs is an integer, and thus to meet a feature of 0.4%, a gelatin constituted of 251 amino acids should include at least two RGD sequences. Preferably, the RGD-enriched recombinant gelatin includes at least two RGD sequence per 250 amino acids, more preferably at least three RGD sequences per 250 amino acids, and most preferably at least four RGD sequences per 250 amino acids.

In a further embodiment, the gelatin is an RGD-enriched gelatin including at least four RGD motifs, preferably at least 6 RGD motifs, more preferably at least 8 RGD motifs, even more preferably at least 12 to 16 RGD motifs.

The recombinant gelatins used in the present invention are preferably derived from collagenous sequences. Nucleic acid sequences encoding collagenous sequences have been generally described in the art (for example, see Fuller and Boedtker (1981) Biochemistry 20: 996-1006; Sandell et al. (1984) J Biol Chem 259: 7826-34; Kohno et al. (1984) J Biol Chem 259: 13668-13673; French et al. (1985) Gene 39: 311-312; Metsaranta et al. (1991) J Biol Chem 266: 16862-16869; Metsaranta et al. (1991) Biochim Biophys Acta 1089: 241-243; Wood et al. (1987) Gene 61: 225-230; Glumoff et al. (1994) Biochim Biophys Acta 1217: 41-48; Shirai et al. (1998) Matrix Biology 17: 85-88; Tromp et al. (1988) Biochem J 253: 919-912; Kuivaniemi et al. (1988) Biochem J 252:633640; and Ala-Kokko et al. (1989) Biochem J 260: 509-516).

Recombinant gelatins enriched in RGD motifs may also be prepared by, for example, the general methods described in US 2006/0241032A.

For pharmaceutical and medical uses, recombinant gelatins including amino acid sequences closely related to or identical to amino acid sequences of natural human collagens are preferable. More preferably, the gelatin includes one or more (for example, repeated) amino acid sequences found in natural human collagen, particularly, such a sequence which includes an RGD motif (in order to create an RGD-enriched recombinant gelatin). The percentage of RGD motifs in such a selected sequence depends on the selected length of the selected sequence and the selection of a shorter sequence inevitably results in a higher RGD percentage in the final recombinant gelatin. A selected amino acid sequence can be repetitively used to provide a recombinant gelatin having a higher molecular weight than a natural gelatin. Further, a recombinant gelatin which is non-antigenic and RGD-enriched (compared to natural gelatins) may be obtained.

In this manner, in a preferred embodiment, the recombinant gelatin includes a natural human gelatin sequence or a part thereof. Preferably, the recombinant gelatin is an RGD-enriched gelatin including (or constituted of at least 80%) at least 80% of one or more parts of one or more natural human gelatin amino acid sequences. Preferably, each of such parts of human gelatin sequences has a length of at least 30 amino acids, more preferably at least 45 amino acids, and most preferably at least 60 amino acids, for example, 240 or less, preferably 150 or less, and most preferably 120 or less amino acids, each part preferably containing one or more RGD sequences. Preferably, the RGD-enriched recombinant gelatin includes (or is constituted of) one or more parts of one or more natural human collagen sequences.

An example of a suitable source of the recombinant gelatin which may be used to prepare the sheets of the embodiments of the present invention is human COL1A1-1. A part of 250 amino acids including an RGD sequence is described in WO04/085473A. The RGD sequences in the recombinant gelatin can adhere to specific receptors on cell surfaces called integrins.

The RGD-enriched recombinant gelatins may be obtained by the recombinant methods described in, for example, EP0926543A, EP1014176A, or WO01/034646A, particularly, in the Examples of the first two mentioned patent publications. The preferable method for producing an RGD-enriched recombinant gelatin includes starting with a natural nucleic acid sequence encoding a part of the collagen protein that includes an RGD amino acid sequence. By repeating this sequence an RGD-enriched recombinant gelatin may be obtained.

In this manner, the recombinant gelatins can be obtained by expression of a nucleic acid encoding such gelatins by a suitable microorganism. The method can suitably be carried out with a fungal cell or a yeast cell. Suitably, the host cell is a high expression host cells like *Hansenula, Trichoderma, Aspergillus, Penicillium, Saccharomyces, Kluyveromyces, Neurospora* or *Pichia*. Fungal and yeast cells are preferred to bacteria since the fungal and yeast cells are less susceptible to improper expression of repetitive sequences. Most preferably, the host does not have a high level of proteases that attack the gelatin structure being expressed. In this respect, *Pichia* or *Hansenula* offer examples of a very suitable expression system. Use of *Pichia pastoris* as an expression system is disclosed in EP0926543A and EP1014176A. The microorganism may be free of active post-translational processing mechanism such as in particular hydroxylation of proline and also hydroxylation of lysine. Alternatively, the host system may have an endogenic proline hydroxylation activity by which the gelatin is hydroxylated in a highly effective manner.

In another embodiment, the recombinant gelatin has a higher glass transition temperature (Tg) than a natural gelatin, for example, Tg higher than 170° C., particularly, higher than 180° C., more particularly, higher than 190° C. Recombinant gelatins having a higher Tg than the natural gelatin are described in WO05/011740A.

In a further embodiment, the recombinant gelatin has less glycosylation than a natural gelatin, for example, a glycosylation of less than 2% by mass, preferably less than 1% by mass, more preferably less than 0.5% by mass, particularly less than 0.2% by mass, and more particularly less than 0.1% by mass. In a preferred embodiment, the recombinant gelatin is free from glycosylation.

The degree or % by mass of glycosylation refers to the total carbohydrate mass per unit mass of the gelatin, as determined by, for example, matrix assisted laser desorption ionization mass spectrometry (MALD-TOF-MS) or by the titration method by Dubois. The term "glycosylation" refers not only to monosaccharides, but also to polysaccharides, for example, di-, tri-, and tetra-saccharides.

There are various methods for ensuring that glycosylation is low or absent from the gelatin. Glycosylation is a post-translational modification, whereby carbohydrates are covalently attached to certain amino acids of the gelatin. Thus, both the amino acid sequence and the host cell (and enzymes, particularly, glycosyltransferases) in which the amino acid sequence is produced determine the degree of glycosylation. There are two types of glycosylation: N-glycosylation begins with linking of GlcNAc (N-actylglucosamine) to the amide group of asparagines (N or Asn) and O-glycosylation commonly links GalNAc (N-acetylgalactosamine) to the amino acid serine (S or Ser) or threonine (T or Thr).

Accordingly, the degree of glycosylation of the gelatin can controlled and particularly reduced or prevented by selecting an appropriate expression host, and/or by modifying or selecting sequences which lack consensus sites recognized by glycosyltransferases of the host.

Chemical synthesis of a gelatin can also be used to prepare a gelatin which is free from glycosylation. Also, a recombinant gelatin which includes glycosylation may be treated after production to remove all or most of the carbohydrates or an unglycosylated gelatin may be separated from a glycosylated gelatin using known methods.

In a further preferred embodiment, less than 10%, more preferably less than 5% of the amino acid residues of the gelatin are hydroxyproline residues. Preferably, the gelatin is free from hydroxyproline residues. It is also preferable that the gelatin is free of hydroxylated amino acid residues.

In another embodiment the gelatin has an isoelectric point of at least 5 (for example, 5 to 11), preferably more than 6 and most preferably more than 7. The object of the aforementioned isoelectric points is to provide a gelatin which has a net positive charge under physiological conditions. Without being bound by any theory, the net positive charge is thought to aid the attraction, interaction and binding of cells to the sheet and thereby enhance cell proliferation in a case where the sheet of the embodiment of the present invention is used for wound repair.

In the sheet of the embodiment of the present invention, at least half of the chambers are spherical, and/or at least half of the chambers have a diameter within ±30% of an average chamber diameter. In the sheet of the embodiment of the present invention, the average chamber diameter is less than 100 µm.

Preferably, the sheet further includes a network of pores which interconnect the chambers and provide passageways for live cells to enter the chambers. Preferably, the network of pores is such that at least half (at least 50%), more preferably at least 75%, particularly at least 90% of the chambers are connected to at least one other chamber present in the sheet.

Preferably, the chambers includes porous walls (for example, walls which include holes) through which cells may enter and to allow for nutrient diffusion, for example, through the aforementioned network of pores. Preferably, the pores and the holes in the chamber walls have an average diameter of at least 1 µm, and more preferably at least 5 µm.

Preferably, at least half, more preferably at least 75%, particularly, at least 80% of the chambers have a diameter within ±30% of the average chamber diameter (that is, 70% to 130% of the average chamber diameter).

Preferably, at least 75% and particularly at least 80% of the chambers are spherical.

Preferably, at least half, more preferably at least 75%, and particularly at least 80% of the chambers have concave walls.

The average chamber diameter is less than 100 µm, preferably 95 µm or less, and more preferably 90 µm or less.

Thus, the gelatin present in the sheets of the embodiment of the present invention preferably provides a scaffold defining the walls of the chambers and pores. Cells or pharmaceutical substances may enter the chambers via the pores.

Perfect spheres have an aspect ratio of 1:1 and are defined by a single radius. The spherical chambers in the present invention may have an irregular shape as long as the chambers are generally spherical and mostly have concave walls. The aspect ratio of the chambers is preferably 1:1 to 4:1, preferably 1:1 to 3:1, and particularly 1:1 to 2:1. Thus, the spherical chambers preferably have a spherical cross section (for example, like a soccer ball), an ellipsoidal cross section (for example, like a rugby ball), and even potato-shaped chambers are possible.

The gelatin sheet may include components other than a gelatin, such as other polymers, biodegradable polymers, bio-polymers, and softeners.

The gelatin sheets of the embodiments of the present invention may be of any shape depending on the geometry of substrate or mold. The process of the present invention is particularly suitable for producing a flat sheet by using a glass or Teflon (registered trade mark) plate. Thus, the sheets of the embodiments of the present invention are preferably flat films or sheets.

The sheets of the embodiments of the present invention preferably have a thickness of 20 µm to 2 cm, more preferably 50 µm to 1 cm, and particularly 75 µm to 300 µm.

The cross-sectional area of the largest surface of the sheets of the embodiments of the present invention is preferably at least 0.1 $cm^2$, more preferably at least 1 $cm^2$, and particularly at least 100 $cm^2$.

The sheets of the embodiments of the present invention may be produced by any suitable method, for example, by a method which provides a second aspect of the present invention and includes the steps of:

(a) mixing a composition including water, a gelatin, a water-immiscible liquid, and an emulsifying agent to obtain an emulsion;

(b) casting the emulsion having a temperature higher than a temperature at which the gelatin present in the composition forms a gel (that is, a temperature higher than the gelation point of the gelatin) onto a support;

(c) cooling the emulsion present on the support to a temperature lower than a gelation point of the gelatin;

(d) removing the water-immiscible liquid from the gelatin by, for example, washing the gelatin using a suitable solvent, such as acetone, but not limited; and (e) drying the gelatin to provide a porous gelatin sheet.

The above steps (a) to (e) are preferably cell-free steps. That is, the method of a preferable embodiment of the present invention characterized by cell-free.

The pH of the composition used in step (a) is preferably in a range of 3 to 11 and more preferably in a range of 4 to 8. The composition used in step (a) includes an emulsifying agent having a hydrophilic-lipophilic balance ("HLB") of 9 or more, particularly 10 or more, and more particularly, 13 to 19. Two or more emulsifying agents may be used. Examples of suitable emulsifying agents include the following:

PEG 400 monooleate polyoxyethylene monooleate (HLB 11.4),

PEG 400 monostearate polyoxyethylene monostearate (HLB 11.6),

PEG 400 monolaurate polyoxyethylene monolaurate (HLB 13.1), potassium oleate (HLB 20.0), sodium lauryl sulfate (HLB 40), sodium oleate (HLB 18), Myrj (registered trade mark) 52 (polyoxyethylene stearic acid, HLB 17), Brij (registered trade mark) 58 (polyoxyethylene cetyl alcohol, HLB 16), Tween (registered trade mark) 20 (polyoxyethylene sorbitan monolaurate, HLB 16.7), Tween (registered trade mark) 21 (polyoxyethylene sorbitan monolaurate, HLB 13.3), Tween (registered trade mark) 40 (polyoxyethylene sorbitan monopalmitate, HLB 15.6), Tween (registered trade mark) 60 (polyoxyethylene sorbitan monostearate, HLB 14.9), Tween (registered trade mark) 61 (polyoxyethylene sorbitan monostearate, HLB 9.6), Tween (registered trade mark) 65 (polyoxyethylene sorbitan tristearate, HLB 10.5), Tween (registered trade mark) 80 (polyoxyethylene sorbitan monooleate, HLB 15.0), Tween (registered trade mark) 81 (polyoxyethylene sorbitan monooleate, HLB 10.0), and Tween (registered trade mark) 85 (polyoxyethylene sorbitan trioleate, HLB 11.0).

Among the above emulsifying agents, particularly preferable are Tween (registered trade mark) 80, Tween (registered trade mark) 40, Myrj (registered trade mark) 52, and Brij (registered trade mark) 58, and combinations including two or more thereof.

In the present invention, preferably, a single emulsifying agent can be used and one emulsification step can be performed.

Suitable water-immiscible liquids which may be used in step (a) include alkyl acetates (for example, ethyl acetate), hydrocarbons (for example, hexane, heptane, cyclohexane, toluene, xylene, or the like), halogenated hydrocarbons (for example, methylene chloride, monochlorobenzene, dichlorobenzene, or the like) and oils (for example, vegetable oil (for example, corn oil), paraffin oil, or industrial oil) and combinations including two or more of the water-immiscible liquids. A particularly preferable water-immiscible liquid is corn oil.

Typically, the emulsion includes two phases: a water-immiscible phase and an aqueous phase.

Preferably, step (a) is performed such that the volume amount of the water-immiscible phase is equal to or greater than the volume amount of aqueous phase, for example, greater than by a factor of two or more.

If desired, the method of the embodiment of the present invention further includes a step of cross-linking the gelatin during and/or after step (b). Such cross-linking may be chemical, for example, using a cross-linking agent, or more preferably thermal cross-linking, for example, dehydrothermal cross-linking.

The gelatin can be cross-linked via, for example, functional groups present in the gelatin reacting together to form an ionic or covalent bond, for example, the amino groups of lysine can cross-link with the carboxyl groups of glutamic acid and/or aspartic acid of the gelatin or the gelatin may be chemically modified such as an acrylated gelatin.

Suitable cross-linking agents for chemical cross-linking are preferably cross-linking agents that do not elicit toxic or antigenic effects when released during biodegradation. Suitable cross-linking agents include, for example, one or more of glutaraldehyde, water-soluble carbodiimides, bisepoxy compounds, formalin, 1-ethyl-3-(3-dimethylaminopropyl) carbodiimide, bis-hydroxy-succinimides, glycidyl ethers such as alkylene glycol diglycidyl ethers or polyglycerol polyglycidyl ether, diisocyanates such as hexamethylene diisocyanate, diphenylphosphorylazide, D-ribose, genipin, and combinations including two or more thereof. Cross-linking techniques are also described by Weadock et al., in Evaluation of collagen cross-linking techniques (Biomater. Med. Devices Artif. Organs, 1983-1984, 11 (4): 293-318). In a preferred embodiment, water-soluble 1-ethyl-3-(3-dimethylaminopropyl)carbodiimide (EDC) is used. In another preferred embodiment, hexamethylenediisocyanate is used as cross-linking agent. Other suitable cross-linking agents include reactive triazines, for example, cyanuric chloride and dichlorohydroxy-triazine. Other cross-linking compounds include divinyl sulfones, dianhydrides, bifunctional imidates diepoxides or dimaleiimidines. It is also possible to use bifunctional cross-linking agents that have different reactive groups such as a bifunctional cross-linking compound including an epoxide and an anhydride group in one molecule.

Also, useful are enzymatic cross-linking agents, for example, transglutaminase.

The cross-linking agents may have more than two functional groups, for example as in cyanuric chloride (3 functional groups) and in compounds including two epoxides and an anhydride group. Such cross-linking agents typically react with amine and/or sulphydryl groups present in amino acids of the gelatin.

If desired, more than one cross-linking agent may be used. Cross-linking may start spontaneously when the cross-linking agent contacts the gelatin, or after adjusting, for example, pH, or by photo initiation or after using other activation mechanism.

A particularly useful cross-linking agent is glutaraldehyde, which cross-links two lysine residues. Another suitable biocompatible cross-linking agent is 1-ethyl-3-(3-dimethylaminopropyl)carbodiimide (EDC), which couples an amine group and a carboxyl group. Also, hexamethylenediisocyanate may be used as cross-linking agent.

Dehydrothermal cross-linking induces cross-linking by condensation of amine and carboxyl groups present in the gelatin to form amide groups. The dehydrothermal cross-linking is preferably performed at a temperature higher than 120° C. and in vacuum.

In order to contribute to sheet formation, the gelatin preferably includes at least two lysine residues. Preferably, the gelatin is a recombinant gelatin including at least 3, at least 4, 5, 6, 7, 8, 9, 10, 11, or at least 12 lysine residues. In a further embodiment, the gelatin includes, in addition to the at least two lysine residues, at least two amino acid residues selected from aspartic acid and glutamic acid. More preferably, the gelatin includes at least 3, at least 4, 5, 6, 7, 8, 9, 10, 11, or at least 12 aspartic acid and glutamic acid residues, preferably in addition to the at least two lysine residues.

In order to assist with the formation of a porous gelatin sheet in which at least half of the chambers are spherical and/or at least half of the chambers have a diameter within ±30% of the average chamber diameter, the gelatin preferably includes lysine, aspartic acid and/or glutamic acid distributed along the length of the gelatin molecules. Thus, in one embodiment, each stretch of 50 amino acids present in the gelatin includes at least one, preferably at least two lysine residues or at least one aspartic acid or glutamic acid residue, preferably at least two aspartic acid or glutamic acid residues, or at least one lysine residue and at least one aspartic acid or glutamic acid residue. Preferably, each stretch of 40 amino acids (more preferably each stretch of 25 amino acids) present in the gelatin includes at least 1 lysine residues and/or at least one aspartic acid or glutamic acid residue.

Preferably, the gelatin includes cross-linkable amino acid residues which are not adjacent to each other, for example, cross-linkable amino acid residues which are separated by at least 5 amino acids, more preferably by at least 10 amino acids, which are not cross-linkable. Cross-linkable amino acid residues include a primary amine group (in addition to the primary amine group typically used to form an amide bond in protein backbone), —SH and/or carboxylic acid group (in addition to the carboxylic acid group typically used to form an amide bond in protein backbone).

The gelatin is preferably a recombinant gelatin which includes a higher percentage (%) or number of lysine residues than in a natural gelatin, particularly due to assistance for subsequent cross-linking.

Many cross-linking agents bind to lysine residues and/or N-terminal amines. Natural gelatins typically contain 25 to 27 lysine residues and 112 to 133 glutamic and aspartic acid residues per 1,000 amino acid residues. In the recombinant gelatins used in the present invention, the number of lysine residues can be reduced to, for example, equal to or less than about 20, 15, 10 or 5 lysine residues per 1,000 amino acid residues or increased to, for example, equal to or more than about 30, 40 or 50 lysines per 1,000 amino acid residues, if desired.

The number of glutamic or aspartic acid residues present in the gelatins used in the present invention can be decreased to, for example, equal to or less than about 100, 90, 80, 70, 60, 50, 40, 30, 20, 10 or 5 residues per 1,000 amino acid residues or can be increased to, for example, equal to or more than 150 residues per 1,000 amino acid residues, if desired.

If desired, some or all of the glutamine and asparagine residues present in the gelatin can be de-aminated, converting the residues to aspartic acid and glutamic acid residues.

In one embodiment, the gelatin is cross-linked by a method including contacting the gelatin with 0.02 to 1.0 mmol of a cross-linking agent per gram of the gelatin. For example, about 0.02, 0.05, 0.1, 0.25, 0.5, 0.6, 0.7, 0.8, 0.9, 1.0, 2.0, 3.0, 4.0 and 5.0 mmol of a cross-linking agent per gram of the gelatin may be used.

Thus, the number of cross-linkable amino acid residues can be used together with the amount of cross-linking compound that is used to customize the physical properties of the sheet. A high number of cross-linkable residues and/or a high concentration of cross-linking compound can yield robust sheets that are particularly useful for applications where the sheets are exposed to mechanical stress. A lower number of cross-linkable amino acid residues and/or a low concentration of cross-linking compounds can yield sheets that are more easily deformable and are particularly suitable for minimally invasive delivery techniques and for pharmaceutical applications.

Dehydrothermal cross-linking is preferable because this cross-linking avoids potential chemical contamination of the gelatin which is particularly desirable in a case where the sheets are intended for use in medical applications.

The cross-linking degree also affects the time it takes for the gelatin sheets to dissolve or be degraded in the body. It is thus possible to control the dissolution or degradation rate of the sheets for the intended application.

In step (a), the volume:volume ratio of the water to the water-immiscible liquid is preferably in the range 5:1 to 1:10, more preferably 1:1 to 1:5, and particularly 2:3 to 1:3.

The composition used in step (a) (and the resulting emulsion) preferably includes:

1% to 15% by mass, more preferably 1.5% to 10% by mass, and particularly 3% to 5% by mass of the gelatin;

10% to 70% by mass, more preferably 20% to 50% by mass, and particularly 30% to 40% by mass of the water;

20% to 90% by mass, more preferably 40% to 80% by mass, and particularly 50% to 70% by mass of the water-immiscible liquid; and 0.5% to 20% by mass, more preferably 1% to 10% by mass, and particularly 2% to 6% by mass of the emulsifying agent.

Step (a) is preferably performed at a temperature in the range 10° C. to 100° C., more preferably 20° C. to 80° C., and particularly 30° C. to 60° C.

The mixing performed in step (a) may be performed by any suitable method, for example by shaking or stirring. Preferably, the mixing is performed by stirring, particularly stirring at a rate of 20 to 5,000 revolutions per minute ("rpm"), more preferably 200 to 1,000 rpm and particularly 250 to 600 rpm, particularly in a case of using a dissolver-type stirrer.

In step (b), the obtained emulsion is cast on a support at a temperature at which the gelatin present in the composition is not in the form of a gel, for example, the emulsion used in step (b) has a temperature of at least 3° C., more preferably at least 5° C. or 10° C. higher than the gelation point of the gelatin present in the composition. The support may be, for example, a non-porous mold (for example, made of Teflon (registered trade mark) or a plastics material) or a flat non-porous sheet (for example, glass plate).

The cooling performed in step (c) may be passive or active. For example, passive cooling may be provided by simply allowing the emulsion to cool naturally to a temperature at which the gelatin present in the composition solidifies/forms a gel. Cooling may be provided using a cooling means (for example, ice, cool water or by placing the product of step (b) in a refrigerator) for lowering the temperature at a controlled cooling rate or without control. Active cooling is useful for adjusting the properties of the final sheet.

However, preferably, step (c) is performed such that the emulsion cools at a rate of 0.1 to 20° C./min and more preferably 1 to 10° C./min. Such cooling rates can provide sheets having particularly useful properties. For example, in a case where step (b) is performed using an emulsion having a temperature of about 60° C., a preferable cooling rate would be 1.8° C./min. After 30 minutes, the resultant sheet has a final temperature of 6° C. The cooling rate may be linear or not linear.

In step (d), the water-immiscible liquid may be removed from the gelatin by, for example, washing the gelatin with a solvent having a lower boiling point than the water-immiscible liquid, and for example, corn oil (high boiling point) may be washed off using acetone (low boiling point). The liquid used to wash off the water-immiscible liquid then evaporates off due to its relatively low boiling point. The drying method used is not important and includes, for example, drying in an oven, by blowing warm air, drying in vacuum and simply allowing the resultant sheet to dry naturally.

Preferably, the method of the embodiment of the present invention is performed under sterile conditions.

In consideration of the foregoing, a method according to the second aspect of the present invention preferably has the following features:

(i) the composition used in step (a) includes
3% to 5% by mass of the gelatin,
30% to 40% by mass of the water,
50% to 70% by mass of the water-immiscible liquid, and
2% to 6% by mass of the emulsifying agent, (ii) the mixing in step (a) is performed by stirring at a rate of 250 to 600 revolutions per minute;

(iii) in step (a), the volume:volume ratio of the water to the water-immiscible liquid is in the range 2:3 to 1:3;

(iv) the emulsion cast onto the support in step (b) has a temperature higher than the gelation point of the gelatin present in the composition;

(v) preferably, step (c) is performed such that the emulsion present on the support cools at a rate of 1 to 10° C./min; and (vi) if desired, this method further includes a step of cross-linking the obtained porous gelatin sheet, preferably by dehydrothermal cross-linking.

According to the preferable aspect of the present invention the gelatin sheets of the first aspect of the present invention have one or more of the following features:

(a) surface pores having a minimum average diameter of at least 1 μm, for example, at least 3 μm, even more preferably at least 5 μm;

(b) a porosity of at least 50 vol %, for example, 51% to 95 vol %, and particularly 60% to 90 vol %;

(c) a density of 0.04 to 0.50 g/cm³, for example, 0.06 to 0.25 g/cm³, and particularly 0.1 to 0.2 g/cm³;

(d) a volume of 2 to 25 cm³/g, for example, 4 to 17 cm³/g, and particularly 5 to 10 cm³/g;

(e) an average chamber diameter less than 100 μm and preferably at least 80% of the chambers have a diameter within ±30% of the average chamber diameter; and (f) a network of pores which interconnect the chambers, preferably such pores having an average diameter of at least 1 μm, for example, at least 3 μm and preferably at least 5 μm.

The average diameter of the chambers and pores may be measured by analysis of Scanning electron microscopy images (for example, using a Jeol JSM6330F) and by microcomputer Ted tomography (CT) (Skyscan1172 MicroCT apparatus with VGStudio MAX 2.2 software (manufactured by Bruker)).

The average porosity of the sheet may be determined by performing the following calculation shown in Equation (1) as follows:

$$P = (pvl/V) \times 100\% \qquad \text{Equation (1)}$$

In the equation:
P is the average porosity of the sheet;
pvl is the average total space volume inside the sheet; and
V is the average total volume of the sheet.

pvl may be measured by microCT measurement (for example, using Skyscan1172 MicroCT apparatus (manufactured by Bruker)) or by mercury intrusion (applicable in a case where pores are interconnected).

Another method for calculating the average porosity (P) of the sheet is from the measurement of the mass of a known volume of the sheet and use of the density of the gelatin (1.34 g/cm³). For example, the mass of a 1 cm³ sheet is measured and the average porosity is calculated by Equation (2):

$$P = (1 - W/d) \times 100\% \qquad \text{Equation (2)}$$

In the equation:
P is the average porosity of the sheet;
W is the mass of 1 cm³ of the sheet; and
d is density of the gelatin (1.34 g/cm³).

The gelatin sheets of the embodiments of the present invention preferably have one or more of the features (a) to (f) described above and/or one or more of the features described below. The porous gelatin sheets may be obtained by the method described above.

The aforementioned features (a) to (f) apply to both the cross-linked and uncross-linked sheets of the embodiments of the present invention.

The above-described method may be used to provide gelatin sheets having a three-dimensional structure which is quite different from film sheets currently available in the marketplace. More specifically, the method can be used to provide the porous gelatin sheets described in the first aspect of the present invention.

According to a third aspect of the present invention, there is provided a composite including the porous gelatin sheet according to the first aspect of the present invention and live cells.

Typically, the live cells are present in the chambers and/or pores of the embodiment of the sheet according to the present invention, particularly, in the chambers. If desired, the composite further includes one or more nutrients for the live cells.

The types of live cells which may be present in the composite of the embodiment of the present invention include, without limitation, human and animal cells. For example, skin cells can be used and the obtained composite can be used for treating various types of injuries to the skin. Another example is myoblasts (muscle cells) which can be used in treatment of, for example, myocardial infarction. One more example is hepatocytes which can be used to render toxic substances in liver lesions harmless. In a preferred embodiment, the live cells are stem cells, for example, embryonic stem cells, hematopoietic stem cells, neuronal stem cells, epidermal stem cells, and mesenchymal stem cells. Other cells which may be used include multipotent, endothelial, progenitor and bone marrow-derived cells.

Live cells are cells which are capable of proliferating in a case where fed nutrients under the conditions in which the cells normally exist in the human or animal body from which they are derived or in which they are intended to be used.

The composite of the embodiment of the present invention may be prepared by culturing the sheets of the embodiment of the present invention with the desired cells.

The specific nutrients used to make the cells proliferate are typically selected to match the cells being grown. Many nutrient formulations are commercially available and include Dulbecco's modified eagle's medium (DMEM), basal medium eagle (BME), DMEM/F12 media, Ham's F-10 and F-12 Media, medium 199, MEM, Ames' media, BGJb medium (Fitton-Jackson Modification), Click's medium, CMRL-1066 medium, Fischer's medium, Glascow Minimum Essential Medium (GMEM), Iscove's Modified Dulbecco's Medium (IMDM), L-15 Medium (Leibovitz), McCoy's 5A Modified Medium, NCTC Medium, Swim's S-77 Medium, Waymouth Medium and William's Medium E and RPMI 1640 Media.

The sheet and composite of the first and third aspects of the present invention can be used for various purposes, for example, as cell carriers for regenerative medicine therapies or as a scaffold for repairing tissue damage. Thus, the sheets of the first aspect of the can be infused with live cells to give a composite according to the third aspect of the present invention and then used to carry or to culture artificial skin, artificial organs, fatty tissue, muscle, blood vessels and the like. The sheet and composite can be used both as carrier for cells in cell cultures and as carriers for existing cells for the production of a desirable substance before or after implantation into a human or animal body. The cells can be either the hosts' own (autologous) cells or cells from another source (characteristic of the species or foreign to the species). In some cases, the cells can be the desirable product, for example, initial stages of fat cells (preadipocytes) attached on the carrier which can proliferate after implantation so as to be converted into fat cells later.

The sheets and composites of the embodiments of the present invention are particularly useful in the fields of plastic surgery and also in toxicity and drug screening assays. In the latter cases, the sheet according to the first aspect of the present invention may be colonized with live cells suitable to be used for toxicity or drug screening. The sheets of the embodiments of the present invention advantageously allows the cells to organize in a more natural spatial conformation, which is representative of the cell organization found in living organisms. It is also possible to implant the sheets according to the embodiments of the present invention in a human or animal body without having first infused the sheet with live cells. After implantation of the sheet into the human or animal body, neighboring cells in the body migrate into and colonize the sheet, for example, by settling in the chambers and/or pores and then proliferating. After the implanted sheet is dissolved, the colonized cells form a structure corresponding to the implant.

The present invention will be described by the following Examples which are not limited. The following abbreviations are used.

"RG1" means a 10% by mass of a solid aqueous composition including an RGD-enriched recombinant gelatin (MWT: 51.2 kDa) having a pH of 5.4 and the sequence shown below as SEQ ID No. 1. This RGD-enriched recombinant gelatin was produced based on a nucleic acid sequence that encodes for a part of the gelatin amino acid sequence of human COL1Al-I and modifying this nucleic acid sequence. The used methods are disclosed in EP0926543A, EP1014176A, and WO01/034646A. Thus, RG1 is free from hydroxyproline and includes the following amino acid sequence hereinafter referred to as SEQ ID No. 1.

```
Amino acid sequence of SEQ ID No. 1:
GAPGAPGLQGAPGLQGMPGERGAAGLPGPKGERGDAGPKGADGAPGAPGL

QGMPGERGAAGLPGPKGERGDAGPKGADGAPGKDGVRGLAGPIGPPGERG

AAGLPGPKGERGDAGPKGADGAPGKDGVRGLAGPIGPPGPAGAPGAPGLQ

GMPGERGAAGLPGPKGERGDAGPKGADGAPGKDGVRGLAGPPGAPGLQGA

PGLQGMPGERGAAGLPGPKGERGDAGPKGADGAPGAPGLQGMPGERGAAG

LPGPKGERGDAGPKGADGAPGKDGVRGLAGPIGPPGERGAAGLPGPKGER

GDAGPKGADGAPGKDGVRGLAGPIGPPGPAGAPGAPGLQGMPGERGAAGL

PGPKGERGDAGPKGADGAPGKDGVRGLAGPPGAPGLQGAPGLQGMPGERG

AAGLPGPKGERGDAGPKGADGAPGAPGLQGMPGERGAAGLPGPKGERGDA

GPKGADGAPGKDGVRGLAGPIGPPGERGAAGLPGPKGERGDAGPKGADGA

PGKDGVRGLAGPIGPPGPAGAPGAPGLQGMPGERGAAGLPGPKGERGDAG

PKGADGAPGKDGVRGLAGPPG
```

SEQ ID No. 1 is 571 amino acids in length and includes 12 RGD motifs.

"Tween (registered trade mark) 80" is a polyoxyethylene sorbitan monooleate.

"DMEM" is Dulbecco's Modified Eagle Medium.

EXAMPLES

Example 1

Step (a)—Preparation of First Emulsion

A mixture of RG1 (15 g, 10% by mass of solids), and Tween (registered trade mark) 80 (1.0 g) was heated to 60° C. and kept at the temperature for 15 minutes. The mixture contained water derived from RG1 (including 90% by mass of water). For FS1, a water-immiscible liquid (corn oil, 30 ml) was added to the mixture over 7 minutes while stirring the mixture at 550 rpm. Stirring at 550 rpm was further continued for 3 minutes or longer while keeping the temperature at 60° C. (which is higher than the gelation point of RG1) to obtain a first emulsion. In order to prepare FS1a and FS1b having different average chamber diameters, the stirring rate was adjusted to obtain sheets having predetermined average chamber diameters.

Step (b)—Preparation of Coating

The first emulsion was further cast onto a glass plate at 60° C. in a variety of thicknesses.

Step (c)—Cooling of Coating

The glass plates coated with the various thicknesses of the first emulsion were cooled in a refrigerator at a temperature of 4° C. for 30 minutes, thereby causing RG1 to solidify as porous gelatin sheets on the glass plates.

Step (d)—Removal of Water-Immiscible Liquid

The glass plates having the porous gelatin sheets were transferred to cooled acetone baths. The sheets were washed with fresh acetone several times until the water and corn oil were removed from the sheets. The sheets were then dried in the oven at 60° C.

Optional Step (e)—Cross-linking

The sheets obtained from step (d) were cross-linked by dehydrothermal treatment as follows to obtain cross-linked porous gelatin sheets: the dry sheets obtained from step (d) were put in a Binder VD53 vacuum stove at a temperature of 145° C. under vacuum for 96 hours.

The cross-linked porous gelatin sheets ("Sheet FS1", "Sheet FS1a", and "Sheet FS1b") formed by casting a layer of the first emulsion onto the glass plate as described above had the properties described in Table 1 below.

TABLE 1

Properties of Sheets FS1, FS1a, and FS1b

| Were at least half of chambers spherical? | Did at least half of chambers have diameter within ±30% of average chamber diameter? | Average chamber diameter[1] (μm) | Average porosity (%)[2] | Average density[3] (g/cm³) | Average volume[4] (cm³/g) | |
|---|---|---|---|---|---|---|
| Yes | Yes | 37 | 85% | 0.17 | 6 | FS1 |
| Yes | Yes | 89 | Not measured | Not measured | Not measured | FS1a |
| Yes | Yes | 121 | Not measured | Not measured | Not measured | FS1b |

Notes:
[1]The shape and average diameter of the chambers in Sheets FS1, FS1a, and FS1b were measured by using SEM images and microCT data (using a Skyscan 1172 MicroCT apparatus from Bruker with VGStudio MAX 2.2 software).
[2]The average porosity of Sheet FS1 was measured by Equation (1) described above.
[3]The average density of Sheet FS1 was calculated by measuring the total mass of the 1 cm³ sheet.
[4]The average volume of Sheet FS1 was measured by measuring the volume of 1 g of Sheet FS1.

Examples 2 to 4 and Comparative Example 1

Example 1 was repeated except for the changes indicated in Table 2 below. The properties of the obtained sheets are shown in Table 3:

TABLE 2

| Example | Changes relative to Example 1 | Sheet |
|---|---|---|
| 2 | In step (b), first emulsion was cast onto Teflon plate instead of glass plate at thickness of 900 μm. | Sheet FS2 |
| 3 | In step (b), first emulsion was cast onto Teflon plate instead of glass plate at thickness of 2,500 μm. | Sheet FS3 |
| 4 | In step (b), first emulsion was cast onto Teflon plate instead of glass plate at thickness of 7,500 μm. | Sheet FS4 |

TABLE 3

Properties of Sheets FS2 to FS4 and Comparative Example 1 (Zimmer Dental CollaTape (registered trade mark))

| Example | Sheet | Were at least half of chambers spherical? | Did at least half of chambers have diameter within ± 30% of average chamber diameter? |
|---|---|---|---|
| 2 | Sheet FS2 | Yes (see FIG. 1B) | Yes |
| 3 | Sheet FS3 | Yes (see FIG. 1C) | Yes |
| 4 | Sheet FS4 | Yes | Yes |
| Comparative Example 1 | CollaTape (registered trade mark) from Zimmer Dental | No (see FIG. 2) | No (see FIG. 2) |

| Example | Sheet | Average chamber diameter (μm) | Average porosity (%) | Average density (g/cm³) | Average volume (cm³/g) |
|---|---|---|---|---|---|
| 2 | Sheet FS2 | 85 | 85 | 0.20 | 5 |
| 3 | Sheet FS3 | 78 | 92 | 0.11 | 9 |
| 4 | Sheet FS4 | 76 | 96 | 0.05 | 19 |
| Comparative Example 1 | CollaTape (registered trade mark) from Zimmer Dental | * | Not measured | Not measured | Not measured |

(The average chamber diameter, average porosity, average diameter, average density, and average volume were measured as described above in Example 1.)
* = The average chamber diameter could not be measured as most of the chambers were not spherical.
Sheets FS1 to FS4 and the sheet of the Comparative Example 1 were analyzed by SEM. SEM photographs of Sheets FS1, FS2 and FS3 are shown in FIG. 1A, FIG. 1B, and FIG. 1C respectively and the SEM photograph of Comparative Example 1 is shown in FIG. 2.

Preparation and Testing of Composites

The composites according to the third aspect of the present invention and a composite of Comparative Example were prepared as follows:

Sterilization Step

Each of Sheets FS1 to FS4 was put in saline phosphate buffer (calcium and magnesium-free; abbreviated as "PBS"). After 1 hour at room temperature in the PBS buffer, the sheets were sterilized by autoclaving (without removing the PBS). After the sterilization, the PBS was removed and fresh PBS was added. The sterilization, PBS removal and PBS replacement cycle were repeated three times. Finally the obtained sterilized sheets were stored in DMEM containing 10% fetal bovine serum ("FBS") at 4° C. until being used. The commercially available sheet for Comparative Example 1 (CollaTape (registered trade mark) from Zimmer Dental) was used directly from the sterile packaging without additional sterilization.

Preparation of C2C12 Cells (Muscle Fibroblast Mouse, ATCC CRL 1772)

The C2C12 cells were pre-cultured in DMEM containing 10% FBS in T75 culture flasks and passaged when cells were 50% to 60% confluent and actively proliferating. Then, the cells were rinsed with PBS (1 ml/5 cm²) to remove the DMEM containing 10% FBS. Subsequently, PBS was aspirated. A trypsin/EDTA solution was added to the cells (3 to 4 ml/75 cm²) and the resultant mixture was incubated at 37° C. for 6 minutes. Then, again DMEM containing 10% FBS was added to neutralize the trypsin using 1:2 ratio to the amount of trypsin. The obtained single cell solution was then centrifuged at 125 rpm for 5 minutes at room temperature. The supernatant was aspirated and the live cells within the resultant cell pellet were gently re-suspended in DMEM containing 10% FBS to obtain C2C12 cells. The cell density was measured using a microscope.

Cell Culturing

The C2C12 cells obtained as described above were seeded onto a circular Sheet FS1 of 5 mm diameter and the sheet used in the Comparative Example (CollaTape (registered trade mark) from Zimmer Dental) at a density of $5\times10^5$ cells per circular sheet using a dynamic shaker method. The dynamic shaker method included placing the sheets under evaluation in a suspension of the C2C12 cells and rotating the mixture at 200 rpm for 4 hours, then transferring the sheet under evaluation to a cell culture plate in DMEM containing 10% FBS. Then, the cells were cultured in the presence of the sheet under evaluation for 7 days in DMEM containing 10% FBS. Then, the amount of live cells present within the sheet under evaluation was measured by DNA quantification (CyQuant Picogreen Assay). The results are shown in Table 4.

TABLE 4

| Proliferation Results (evaluated by the picogreen DNA quantification) | |
|---|---|
| Sheet | Cell proliferation score |
| Sheet FS1 | +++ |
| Sheet FS1a | +++ |
| Sheet FS1b | + |
| Sheet FS2 | +++ |
| Sheet FS3 | ++ |
| Sheet FS4 | ++ |
| CollaTape (registered trade mark) | + |

In Table 4, the following scoring system was used.
+++ means very good cell proliferation;
++ means good cell proliferation; and
+ means moderate cell proliferation.

As can be seen from Table 4, the cell proliferation of Sheets FS1, FS1a, and FS2 to FS4 according to the present invention was superior to the cell proliferation of Comparative Example. In addition, Sheet FS1b of which the average chamber diameter was more than 100 μm exhibited low degree of cell proliferation.

SEQUENCE LIST

International Application 17F01330 Method for Producing Porous Gelatin Sheet JP17015990 20170421 —00060080351700874806 Normal 20170421120109201703311209285610_P1AP101_17_4.app Based on International Reception Patent Cooperation Treaty

What is claimed is:

1. A method for producing a porous gelatin sheet including chambers, the method comprising the steps of:
   (a) mixing a composition including water, a gelatin, a water-immiscible liquid, and an emulsifying agent to obtain an emulsion,
   wherein, in step (a), a volume of a water-immiscible phase is equal to or larger than a volume of an aqueous phase;
   (b) casting the emulsion having a temperature higher than a temperature at which the gelatin present in the composition forms a gel onto a support;
   (c) cooling the emulsion present on the support to a temperature lower than a gelation point of the gelatin present in the composition;
   (d) removing the water-immiscible liquid from the gelatin; and
   (e) drying the gelatin to provide a porous gelatin sheet,
   wherein at least half of the chambers are spherical and/or at least half of the chambers have a diameter within ±30% of an average chamber diameter, and the average chamber diameter is less than 100 µm.

2. The method according to claim 1,
   wherein steps (a) to (e) are cell-free steps.

3. The method according to claim 1,
   wherein the emulsifying agent has an HLB of 9 or more.

4. The method according to claim 1,
   wherein the sheet further includes a network of pores which interconnect the chambers and provide passageways for cells to enter the chambers.

5. The method according to claim 1,
   wherein the sheet has a porosity of at least 50 vol %.

6. The method according to claim 1,
   wherein the sheet has an average pore diameter of at least 5 µm.

7. The method according to claim 1,
   wherein the sheet has a density of 0.04 to 0.5 g/cm$^3$.

8. The method according to claim 1,
   wherein the sheet has a volume of 2 to 25 cm$^3$/g.

9. The method according to claim 1,
   wherein the sheet has a porosity of at least 50 vol %, and the sheet includes pores having an average diameter of at least 5 µm,
   (i) at least half of the chambers are spherical, and
      (ii) at least 80% of the chambers have a diameter within ±30% of the average chamber diameter.

10. The method according to claim 1,
    wherein the sheet has a porosity of at least 50 vol %, the sheet includes surface pores having an average diameter of at least 5 µm, and at least half of the chambers have a diameter within ±30% of the average chamber diameter.

11. The method according to claim 1,
    wherein at least 50% of the chambers are spherical.

12. The method according to claim 1,
    wherein the gelatin is a recombinant gelatin.

13. The method according to claim 1,
    wherein the gelatin is a recombinant gelatin having an isoelectric point of at least 5.

14. The method according to claim 1,
    wherein the gelatin is a recombinant gelatin including at least three RGD motifs.

15. The method according to claim 1,
    wherein the gelatin is a recombinant gelatin including at least two lysine residues, the lysine residues are extreme lysine residues, a first extreme lysine residue is a lysine residue that is closest to an N-terminus of the gelatin, a second extreme lysine residue is a lysine residue that is closest to a C-terminus of the gelatin, and the extreme lysine residues are separated by at least 25% of the total number of amino acid residues of the gelatin.

16. A porous gelatin sheet produced by the method according to claim 1.

17. A cell carrier, comprising: the porous gelatin sheet according to claim 16.

18. A scaffold for repairing tissue damage, comprising: the porous gelatin sheet according to claim 16.

19. A composite comprising:
    the porous gelatin sheet according to claim 16; and
    live cells.

* * * * *